(12) United States Patent
Sarmadi

(10) Patent No.: US 6,171,105 B1
(45) Date of Patent: Jan. 9, 2001

(54) DENTAL-RESTORATION LIGHT-CURING SYSTEM

(75) Inventor: Kamran Sarmadi, Arcadia, CA (US)

(73) Assignee: EG&G ILC Technology, Inc., Sunnyvale, CA (US)

( * ) Notice: Under 35 U.S.C. 154(b), the term of this patent shall be extended for 0 days.

(21) Appl. No.: 09/404,265

(22) Filed: Sep. 21, 1999

(51) Int. Cl.$^7$ ............................. A61C 1/00; A61C 3/00
(52) U.S. Cl. ............................................. 433/29
(58) Field of Search .................... 433/29, 215, 226, 433/229

(56) References Cited

U.S. PATENT DOCUMENTS

| | | | |
|---|---|---|---|
| 4,979,180 | * 12/1990 | Muncheryan | 372/92 |
| 5,182,588 | 1/1993 | Maurer et al. | 351/165 |
| 5,344,418 | * 9/1994 | Ghaffari | 606/9 |
| 5,721,465 | 2/1998 | Roberts | 313/46 |
| 5,843,143 | * 12/1998 | Whitehurst | 607/88 |
| 5,879,159 | 3/1999 | Cipolla | 433/29 |
| 6,102,696 | * 8/2000 | Osterwalder et al. | 433/29 |

OTHER PUBLICATIONS

Vol. 2, No. 2, of "inciDENTALs", the Journal for the Dental Assistant and Receptionist, ©1998.

* cited by examiner

*Primary Examiner*—Nicholas D. Lucchesi
(74) *Attorney, Agent, or Firm*—Thomas E. Schatzel; Law Offices of Thomas E. Schatzel

(57) ABSTRACT

A blue-light polymerizing system comprises a xenon arc lamp in which its sapphire window includes a blue-bandpass filter coating. This eliminates any external color filters that would otherwise be necessary for the polymerization of dental composite materials in a patient's mouth. The blue-bandpass filter coating causes the xenon arc lamp to heat an extra 10° C. higher than would otherwise be the case. So a special anode heatsink is fitted in which the front and back halves of each radial fin have been separated, and one of these groups of separated fins has been tilted off normal. Such changes the otherwise laminar airflow through the anode heatsink fins to a turbulent flow that is better able to collect heat and carry it off.

12 Claims, 2 Drawing Sheets

DENTAL-RESTORATION LIGHT-CURING SYSTEM

BACKGROUND OF THE INVENTION

1. Field of the Invention

The invention relates generally to blue-light sources used to polymerize dental restoration composite materials and specifically to light-curing systems that use xenon arc lamps coupled through liquid-filled light guides to a wand.

2. Description of the Prior Art

Up until very recently, dentists universally used catalytically cured resins to fill cavities and restore teeth. Now most such restorative materials are light-cured, wherein exposure to intense light is used to polymerize and harden the fillings. The most energetic light wavelength to use is ultraviolet (UV) light because each UV-photon packs far more energy than do photons of light having longer wavelengths. But UV-light is associated with skin damage and can be hazardous to both dentist and patient alike.

Robert D. Maurer, et al., describes such light-cured materials and the hazards associated with exposure to ultraviolet and other intense light sources in U.S. Pat. No 5,182,588, issued Jan. 26, 1993. Glasses with filter coatings are proposed that absorb UV-light and blue-light to protect the dentist's eyes. This, of course, does nothing to protect the patient's exposed skin or the face and hands of the dentist.

The use of UV-light to polymerize dental composite materials proved to be too hazardous, so now blue-light only systems are used that provide as good, if not superior performance. Several manufacturers of the blue-light cured dental composite materials now exist. These roughly fall into two categories, ones that nominally cure at 430 nanometer light-wavelength, and ones that cure at about 470 nanometers.

A typical short arc lamp comprises an anode and a sharp-tipped cathode positioned along the longitudinal axis of a cylindrical, sealed concave chamber that contains xenon gas pressurized to several atmospheres. U.S. Pat. No. 5,721,465, issued Feb. 24, 1998, to Roy D. Roberts, describes such a typical short-arc lamp. Such Patent is incorporated herein by reference. A typical xenon short-arc lamp is marketed by ILC Technology (Sunnyvale, Calif.) under the CERMAX™ trademark.

Bare, unfiltered xenon arc lamps put out a wide spectrum of light values. Too wide, in fact, for their use in blue-light dental composite material curing systems. Both the 430 and 470 nanometer wavelengths of light will be found in the output of a xenon lamp, and these can be used for polymerization. But many other wavelengths are also produced that must be absorbed as heat by the patients and their teeth. These other wavelengths contribute nothing to the polymerization. The absorbed heat can irritate or worry the patient, and therefore complicate the dentist's job.

Figure 2:
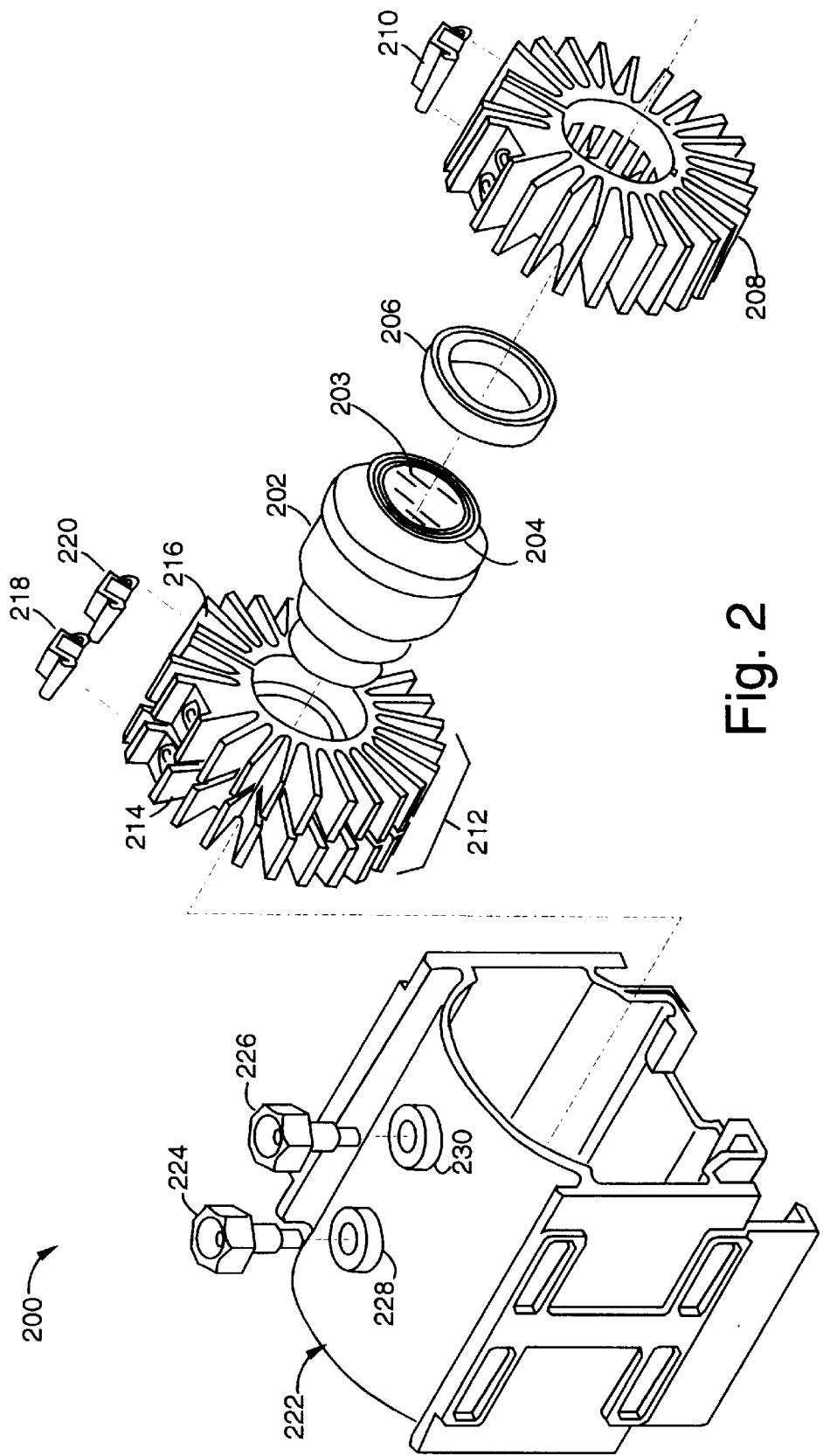

A portable high-power arc-lamp system for composite curing and teeth whitening is described by John Cipolla in U.S. Pat. No 5,879,159, issued Mar. 9, 1999, (Cipolla '159). FIG. 2 of such patent shows the spectral output of an optical blue-green color bandpass filter (127) that is used, i.e., 430–500 nanometers. Such color bandpass filter is mounted external to the lamp and resembles a monocle on a holder. The unfiltered spectral output of a xenon short arc lamp is illustrated in FIG. 3 of Cipolla 159. Such lamps produce significant amounts of infrared energy, so Cipolla suggests that a separate dichroic filter can be inserted between the reflector and light guide to absorb and dissipate the infrared wavelengths.

As it turns out, so much infrared light is output by the xenon arc lamp in prior art blue-light curing systems that the color bandpass filters alone can not handle the heat loads. An infrared pre-filter is needed to spread the heat deposited in the filters between two such filters. Otherwise, the glass on which the filter coatings are deposited will heat up to several hundred degrees Celsius and fracture. As can be expected, these filters add extra cost to the manufacture of such systems.

Another problem in prior art polymerization systems is controlling the dosage of the blue-light radiation applied to polymerize the composite materials. Volume 2, number 2, of "inciDENTALs", the Journal for the Dental Assistant and Receptionist, © 1998, states that the curing lights now in use have output energies that diminish over time. So stand-alone light-meters are suggested to periodically test the intensity of a dentist's curing light. Such suggests that if a reading of "200-300" is obtained, then the recommended curing time should be increased. If the reading is under "200", then the lamp is bad and should be repaired or replaced. This caution indicates that some procedures may, in fact, under-cure or over-cure the dental composite materials because the dosage rate can vary unbeknownst to the dentist.

SUMMARY OF THE PRESENT INVENTION

It is therefore an object of the present invention to provide a blue-light polymerizing system that is less expensive to build compared to conventional designs.

Briefly, a blue-light polymerizing system embodiment of the present invention comprises a xenon arc lamp in which its sapphire window includes a blue-bandpass filter coating. This eliminates any external color filters that would otherwise be necessary for the polymerization of dental composite materials in a patient's mouth. The blue-bandpass filter coating causes the xenon arc lamp to heat an extra 10° C. higher than would otherwise be the case. So a special anode heatsink is fitted in which the front and back halves of each radial fin have been separated, and one of these groups of separated fins has been tilted off normal. Such changes the otherwise laminar airflow through the anode heatsink fins to a turbulent flow that is better able to collect heat and carry it off.

An advantage of the present invention is that a blue-light polymerizing system is provided that is less expensive to manufacture.

Another advantage of the present invention is that a blue-light polymerizing system is provided that uses fewer operating parts.

These and other objects and advantages of the present invention will no doubt become obvious to those of ordinary skill in the art after having read the following detailed description of the preferred embodiment which is illustrated in the drawing figure.

IN THE DRAWINGS

Figure 1:
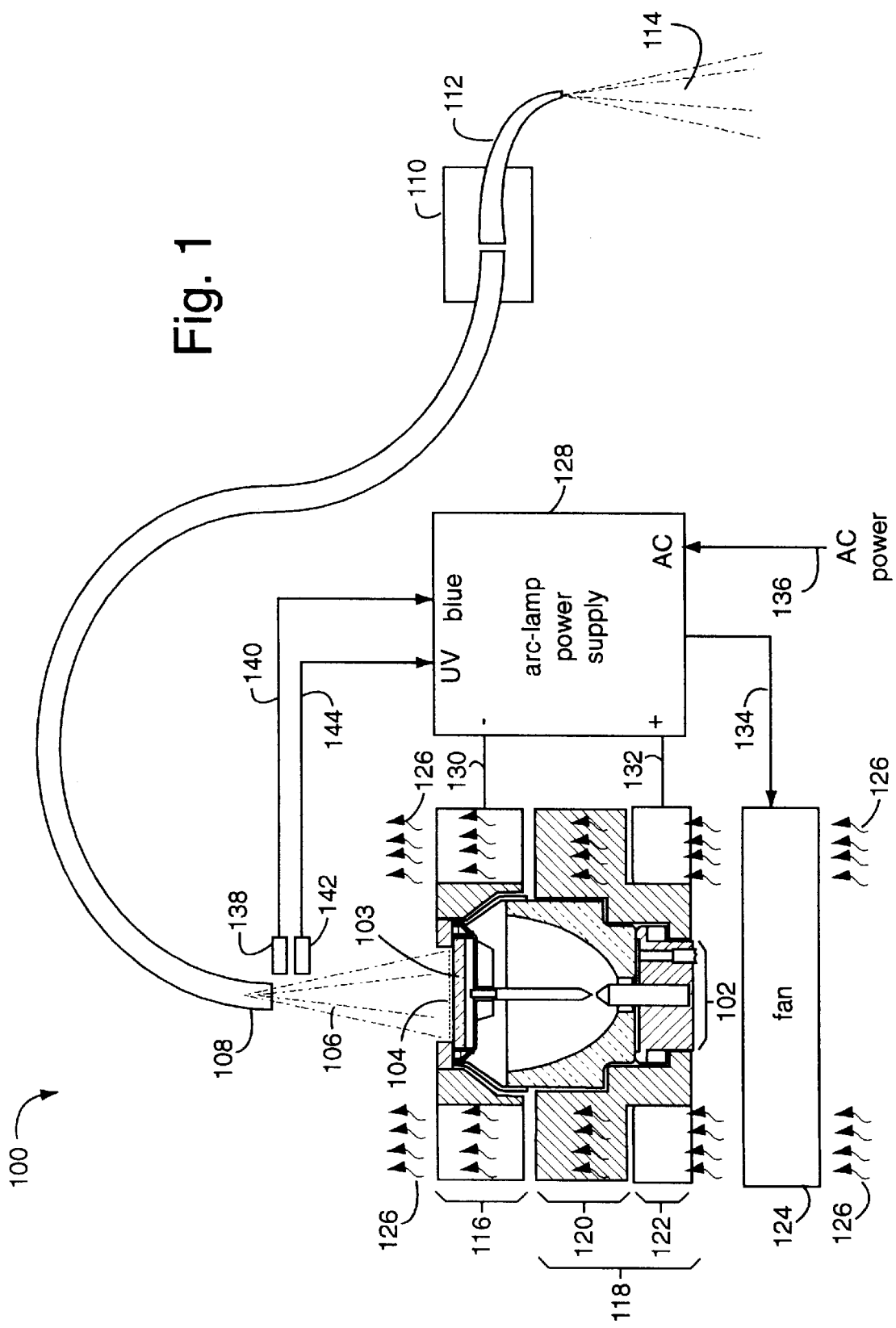

FIG. 1 is a block diagram of a blue-light polymerizing system embodiment of the present invention and shows the xenon arc lamp and its heatsink in cross-section; and FIG. 2 is a perspective diagram that shows a lamp assembly that is similar to the lamp of FIG. 1.

DETAILED DESCRIPTION OF THE PREFERRED EMBODIMENT

FIG. 1 represents a blue-light polymerizing system embodiment of the present invention, referred to herein by the general reference numeral 100. The system 100 includes an elliptical reflector xenon short-arc lamp 102 with a sapphire window 103. A dichroic coating 104 is applied directly to the outside face of the sapphire window 103 to block all but a 400–500 nanometer wavelength (blue) light 106. A flexible liquid-filled light guide 108 has a numerical aperture that allows most all of the blue light 106 to be accepted. A light-wand 110 allows a swivel connection to a detachable and washable probe 112. Such light wand 110 is held by a dentist while the probe 112 is inserted into the mouth of a patient to light-cure a dental composite material, e.g., a tooth filling, with a blue output light 114. In alternative embodiments of the present invention, probe 112 includes color filters that provide psuedo-monochromtic output light 114 at either 430 nanometers or 470 nanometers.

The dichroic coating 104 applied directly to the outside face of the sapphire window 103 causes a great deal of heat to be trapped in the lamp 102 that would otherwise escape as radiated energy. If nothing was done about this extra heating, the lamp 102 would run at least 10° C. hotter. But embodiments of the present invention preferably include a cathode heatsink 116 and anode heatsink 118.

Such dichroic coating 104 can be commercially supplied, e.g., by Deposition Sciences, Inc., a subsidiary of Advanced Lighting Technologies, Inc. (386 Tesconi Court, Santa Rosa, Calif. 95401). The bandpass specification of 400–500 nanometers is well suited for the polymerization of composite dental materials sensitive to light wavelengths of 430±20 nanometers and also others sensitive to light wavelengths of 470±20 nanometers. The bandpass specification of 400–500 nanometers allows the two main varieties of composite dental materials to be used without requiring filter changes. The dichroic coating 104 is preferably applied after the lamp 102 is otherwise fully assembled.

The anode heatsink 118 is an extruded aluminum type that includes a set of front radial fins 120 and rear radial fins 122. Such radial fins are initially attached to one another, but a cut all around the outside halfway up the longitudinal length is made so that one set of fins can be bent over a little. A fan 124 provides a forced air flow 126 that becomes turbulent as it interacts with front radial fins 120 and rear radial fins 122. If the front and rear radial fins 120 and 122 were not separated and one group not bent over, a near laminar air flow would result. Such laminar airflow is not as efficient at taking away heat from the lamp. Tests have shown that even with the heat loads that are added by placing the dichroic coating 104 directly on the sapphire window 103, the net result of the turbulent airflow through the heatsink fins is that the lamp 102 runs as much as 5° C. cooler than a conventional system.

An arc-lamp power supply 128 provides a negative supply 130 and a positive supply 132 to the arc lamp 102 through its heatsinks 116 and 118. A separate power connection 134 powers the fan 124. Input power is provided from an AC utility connection 136.

In alternative embodiments of the present invention, the actual illumination power in the 400–500 nanometer wavelength (blue) light 106 is servo-controlled to maintain a constant level. This helps users by allowing them to always use the recommended light-curing dosage and not having to compensate for aging lamps or having to use external light meters. A 400–500 nanometer wavelength photodetector 138 provides a blue-feedback signal 140 that the power supply 128 uses to adjust the power delivered to the lamp 102. An ultraviolet photodetector 142 provides a UV-feedback signal 144 that is used to shutdown the power supply 128 if too much UV-light is detected. Such could occur if the user installed a xenon lamp 102 that lacked the correct dichroic coating 104. The power supply 128 may preferably also include safety circuits that will shut it down if the lamp 102 draws too much current due to decreased internal impedance caused by shorts, operates with too high a voltage due to increased internal impedance caused by aging, or overheats.

FIG. 2 shows a lamp assembly 200 that is similar to the lamp 102 and its heatsinks 116 and 118 in FIG. 1. The lamp assembly 200 includes a xenon short-arc lamp 202 with a 400–500 nanometer color filter 203 on a sapphire window 204. Such xenon short-arc lamp 202 is similar to those marketed by ILC Technology (Sunnyvale, Calif.) under the CERMAX trademark. A heat collar 206 helps conduct heat away from the cathode end of the lamp to an extruded-aluminum cathode heatsink 208. A clip 210 helps clamp the heatsink 208 tightly onto the lamp 202.

An extruded-aluminum anode heatsink 212 has two longitudinal sets of radial fins 214 and 216. Just after extrusion, such radial fins 214 and 216 are connected and aligned at their outer diameters, but a saw is used to cut them free of each other around the middle waist. One set of such radial fins 214 and 216 are bent over in an axial twist. Such bent over fins cause a turbulence to develop in an axial forced air flow that improves cooling of the lamp 202. A pair of clips 218 and 220 help clamp the anode heatsink 212 tightly onto the anode-end of the lamp 202.

The lamp assembly 200 further includes a housing 222 made of an electrically insulative material, e.g., fiberglass resin. A pair of electrical contacts 224 and 226 fit into contact holes 228 and 230. These hold and complete the electrical circuits to the heatsinks 208 and 212 through to the anode and cathode electrodes of the lamp 202.

Although the present invention has been described in terms of the presently preferred embodiments, it is to be understood that the disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

What is claimed is:

1. A blue-light polymerizing system, comprising:
   a xenon short-arc lamp with an elliptical reflector and a sapphire window;
   a dichroic coating applied to said sapphire window and providing for the transmission of light wavelengths in the range of 400–500 nanometers, and the reflection of other wavelengths of light; and
   a liquid light guide positioned to receive a blue light which is output from the xenon short-arc lamp through the dichroic coating and having a distal end with a light wand;
   wherein, said blue light is emitted from said light wand and useful for polymerizing composite materials in a mouth of a dental patient.

2. The blue-light polymerizing system of claim 1, further comprising:
   an anode heatsink with radially extending cooling fins that are axially aligned with and provide cooling of the xenon short-arc lamp.

3. The blue-light polymerizing system of claim 1, further comprising:
   a cathode heatsink with radially extending cooling fins that are axially aligned with and provide cooling of the xenon short-arc lamp.

4. The blue-light polymerizing system of claim 1, further comprising:
   an anode heatsink with two longitudinal sets of radially extending cooling fins that are all axially aligned with and provide cooling of the xenon short-arc lamp;
   wherein, said two longitudinal sets of radially extending cooling fins are axially twisted with respect to one another such that an axially flowing air current is disturbed from laminar to turbulent flow.

5. The blue-light polymerizing system of claim 1, further comprising:
   a probe that is attached to said light wand and that provides for a selective optical color filtration of light wavelengths of at least one of 430±20 nanometers and 470±20 nanometers.

6. The blue-light polymerizing system of claim 1, further comprising:
   a power supply connected to operate the xenon short-arc lamp; and
   a photodetector sensitive to 400–500 nanometer light wavelengths and positioned to be exposed to said blue light, and providing a feedback signal to the power supply that is used to adjust the electrical power applied to the xenon short-arc lamp in order to maintain a near constant intensity of said blue light.

7. The blue-light polymerizing system of claim 1, further comprising:
   a power supply connected to operate the xenon short-arc lamp; and
   an ultraviolet-light photodetector exposed to said blue light and providing a feedback signal to the power supply that is used to shut-down the electrical power applied to the xenon short-arc lamp if an ultraviolet content of said blue light exceeds a predetermined threshold.

8. A blue-light polymerizing system, comprising:
   a xenon short-arc lamp with an elliptical reflector and a sapphire window;
   a dichroic coating applied to said sapphire window and providing for the transmission of light wavelengths in the range of 400–500 nanometers, and the reflection of other wavelengths of light;
   a liquid light guide positioned to receive a blue light which is output from the xenon short-arc lamp through the dichroic coating and having a distal end with a light wand; and
   an anode heatsink with two longitudinal sets of radially extending cooling fins that are all axially aligned with and provide cooling of the xenon short-arc lamp, wherein, said two longitudinal sets of radially extending cooling fins are axially twisted with respect to one another such that an axially flowing air current is disturbed from laminar to turbulent flow;
   wherein, said blue light is emitted from said light wand and useful for polymerizing composite materials in a mouth of a dental patient.

9. The blue-light polymerizing system of claim 8, further comprising:
   a probe that is attached to said light wand and that provides for a selective optical color filtration of light wavelengths of at least one of 430±20 nanometers and 470±20 nanometers.

10. The blue-light polymerizing system of claim 8, further comprising:
    a power supply connected to operate the xenon short-arc lamp; and
    a photodetector sensitive to 400–500 nanometer light wavelengths and positioned to be exposed to said blue light, and providing a feedback signal to the power supply that is used to adjust the electrical power applied to the xenon short-arc lamp in order to maintain a near constant intensity of said blue light.

11. The blue-light polymerizing system of claim 8, further comprising:
    a power supply connected to operate the xenon short-arc lamp; and
    an ultraviolet-light photodetector exposed to said blue light and providing a feedback signal to the power supply that is used to shut-down the electrical power applied to the xenon short-arc lamp if an ultraviolet content of said blue light exceeds a predetermined threshold.

12. A blue-light polymerizing system, comprising:
    a xenon short-arc lamp with an elliptical reflector and a sapphire window;
    a dichroic coating applied to said sapphire window and providing for the transmission of light wavelengths in the range of 400–500 nanometers, and the reflection of other wavelengths of light;
    a liquid light guide positioned to receive a blue light which is output from the xenon short-arc lamp through the dichroic coating and having a distal end with a light wand;
    an anode heatsink with two longitudinal sets of radially extending cooling fins that are all axially aligned with and provide cooling of the xenon short-arc lamp, wherein, said two longitudinal sets of radially extending cooling fins are axially twisted with respect to one another such that an axially flowing air current is disturbed from laminar to turbulent flow;
    a probe that is attached to said light wand and that provides for a selective optical color filtration of light wavelengths of at least one of 430±20 nanometers and 470±20 nanometers;
    a power supply connected to operate the xenon short-arc lamp;
    a photodetector sensitive to 400–500 nanometer light wavelengths and positioned to be exposed to said blue light, and providing a feedback signal to the power supply that is used to adjust the electrical power applied to the xenon short-arc lamp in order to maintain a near constant intensity of said blue light; and
    an ultraviolet-light photodetector exposed to said blue light and providing a feedback signal to the power supply that is used to shut-down the electrical power applied to the xenon short-arc lamp if an ultraviolet content of said blue light exceeds a predetermined threshold;
    wherein, said blue light is emitted from said light wand and useful for polymerizing composite materials in a mouth of a dental patient.

* * * * *